United States Patent [19]

Yamada et al.

[11] Patent Number: 4,731,241

[45] Date of Patent: Mar. 15, 1988

[54] PERCUTANEOUS PHARMACEUTICALS PREPARATION FOR EXTERNAL USE

[75] Inventors: Masayuki Yamada; Yoshiaki Uda, both of Hyogo, Japan

[73] Assignee: Takeda Chemical Industries, Ltd., Osaka, Japan

[21] Appl. No.: 22,515

[22] Filed: Mar. 9, 1987

Related U.S. Application Data

[63] Continuation of Ser. No. 874,703, Aug. 1, 1986, abandoned, which is a continuation of Ser. No. 611,540, May 17, 1984, abandoned.

[30] Foreign Application Priority Data

May 26, 1983 [JP] Japan ................................. 58-93153
Mar. 23, 1984 [JP] Japan ................................. 59-56923

[51] Int. Cl.$^4$ .................... A61L 31/535; A61L 31/19; A61K 15/03
[52] U.S. Cl. .................................... 514/227; 514/227; 514/557; 514/929; 514/947; 424/449
[58] Field of Search ................. 424/28; 514/227, 557, 514/929, 947

[56] References Cited

U.S. PATENT DOCUMENTS 4,420,470 12/1983 Otsuka et al. .......................... 424/28
4,421,737 12/1983 Ito et al. ................................. 424/28

FOREIGN PATENT DOCUMENTS 059356 9/1982 European Pat. Off. .
3231400 3/1983 Fed. Rep. of Germany .
81902 2/1980 Luxembourg .

OTHER PUBLICATIONS

Merck, p. 815, No. 6120, 9th ed., 1976.
Chem. Absts., 73:25485g, 1970.
Chemical Abstracts, vol. 69, No. 20, 11th Nov. 1968, p. 7512, No. 80150m, Columbus, Ohio, US; J. Miyazaki et al.: "Corticosteriod Ointments, III Solubilities of Corticosteriods in Some Alkylol Amides and Alkyl Amides", & Yakuzaigaku 1966, 26(3), 196–199.

Primary Examiner—J. R. Brown
Assistant Examiner—John W. Rollins, Jr.
Attorney, Agent, or Firm—Wegner & Bretschneider

[57] ABSTRACT

A percutaneous pharmaceutical preparation for external use containing N-ethoxycarbonyl-3-morpholinosydnonimine (molsidomine) and an absorption promoter selected from the group consisting of aliphatic monoalcohols of 10 to 22 carbon atoms, aliphatic monoamides of 8 to 18 carbon atoms and aliphatic monoamines of 10 to 16 carbon atoms gives a high blood concentration of molsidomine over a long time period when applied onto the human skin.

5 Claims, No Drawings

PERCUTANEOUS PHARMACEUTICALS PREPARATION FOR EXTERNAL USE

This application is a continuation of U.S. application Ser. No. 874,703, filed Aug. 1, 1986, which is a continuation of Ser. No. 611,540, filed May 17, 1984, both abandoned.

The present invention relates to a drug for percutaneous absorption which contains N-ethoxycarbonyl-3-morpholinosydnonimine known as the generic name of "molsidomine", and the process for production thereof.

More particularly, the present invention relates to a percutaneous pharmaceutical preparation for external use which is adapted to permit absorption of molsidomine through the skin at an optional application site, without requiring oral administration or parenteral administration, and to thereby allow pharmacological effects of molsidomine to be sustained over a long time period, and the process for production thereof.

Molsidomine is a well-known compound having few side effects and excellent vasodilator activity, and has heretofore been used as a therapeutic agent for the coronary insufficiency, hypertensive heart disease, myocardial infarction, angina pectoris, etc.

In the treatment of these diseases, it is desirable that molsidomine be administered in such a manner that it will be absorbed over a sustained time period and at a quantitative rate such that its blood concentration will consistently be higher than its effective concentration and lower than the critical concentration conducive to the onset of side effect. To meet these requirements, it has, for instance, been proposed and practiced to provide the drug for oral administration in the form of specially coated granules or beads, but this and other measures have not proved fully satisfactory, especially in terms of duration of effect.

Under the circumstances the present inventors explored the possibility to let molsidomine be absorbed through the skin to thereby allow its pharmacological effects to be sustained over a long time period and at the same time, either prevent or mitigate its possible adverse reactions.

By nature, some drugs are readily absorbed through the skin, while others are substantially not absorbed through the skin. Administered alone by the percutaneous route, molsidomine is not well absorbed and, therefore, it cannot attain an effective concentration in the blood by this route. Therefore, some ingenuity is required for promoting the percutaneous absorption of molsidomine. Researches have been done towards solving this problem but no effective percutaneous absorption promoters have been discovered as yet.

In the percutaneous absorption of drugs generally, the horny layer of the skin acts as a barrier to the penetration of drugs, and in the case of a drug which would hardly be absorbed through the skin, it is important to find a means by which the permeability of the horny layer to the drug may be enhanced. For this purpose, there may be contemplated to find an absorption promoter which may be an agent that will soften and make permeable the horny layer, an agent that will expand the hair follicles, or an agent that will change the surface condition of the skin However, even if the properties of the horny layer be improved, it does never mean that all kinds of drugs are percutaneously absorbed. The percutaneous absorbability of drugs depends on, and varies considerably with, their physico-chemical properties and the kinds of bases used for pharmaceutical preparations. It is, thus, acknowledged that there exists no absorption promoter agent that would assure percutaneous absorption of all kinds of drugs [Iyakuhin Kaihatsu Kiso Koza IX, Seizai Sekkei-Ho (Lectures on Fundamentals of Drug Development IX, Drug Design) (1) p. 95–107, published by Chizin Shokan in Japan]. That is to say, we have to search for an individualized absorption promoter for each kind of drug.

For the vasodilator drug molsidomine, the present inventors attempted to promote its percutaneous absorption by adding a variety of compounds which are known to moisturize the horny layer, e.g. sorbitol, glycerin, propylene glycol, etc., and many compounds which are known to soften the horny layer, e.g. salicylic acid, methyl salicylate etc., but none of them proved meaningfully effective. Then, the present inventors attempted at a systematic classification of compounds which could contribute to the percutaneous absorption of molsidomine and performed a series of experiments. As a result, certain aliphatic compounds were found to cause a marked promotion of percutaneous absorption of molsidomine and enable the drug to remain in the blood at a sufficient concentration for the development of its pharmacological effects over a sustained time period. The finding was followed by further investigations, which have resulted in the development of the present invention.

Thus, the present invention relates to a percutaneous pharmaceutical preparation for external use which contains N-ethoxycarbonyl-3-morpholinosydnonimine and at least an absorption promoter selected from the group consisting of aliphatic monocarboxylic acids of 5 to 30 carbon atoms, aliphatic monohydric alcohols of 10 to 22 carbon atoms, aliphatic monoamides of 8 to 18 carbon atoms and aliphatic monoamines of 10 to 16 carbon atoms, and the process for production thereof.

The aliphatic monocarboxylic acids of 5 to 30 carbon atoms include saturated, unsaturated, straight and branched fatty acids. The saturated fatty acids include those having 5 to 30 carbon atoms such as valeric acid, isovaleric acid, carproic acid, oenanthic acid, caprylic acid, pelargonic acid, capric acid, lauric acid, myristic acid, palmitic acid, margaric acid, stearic acid, arachidic acid, behenic acid, lignoceric acid, cerotic acid, montanic acid, melissic acid, etc. Preferred are caprylic acid which contains 8 carbon atoms through behenic acid which contains 22 carbon atoms. Said unsaturated fatty acids include such olefinic acid as octenoic acid which contains 8 carbon atoms through arachidonic acid which contains 20 carbon atoms. Preferred are lauroleic acid which contains 12 carbon atoms through arachidonic acid which contains 20 carbon atoms. The aliphatic monohydric alcohols of 10 to 22 carbon atoms may be saturated or unsaturated. The saturated alcohols include capryl alcohol which has 10 carbon atoms through behenyl alcohol which has 22 carbon atoms. Preferred are lauryl alcohol which has 12 carbon atoms through stearyl alcohol which contains 18 carbon atoms. The unsaturated alcohols include such olefinic monohydric alcohols as decenol which has 10 carbon atoms through docosenyl alcohol which has 22 carbon atoms, preferably those having 12 to 18 carbons. The aliphatic monoamides of 8 to 18 carbon atoms may be saturated or unsaturated The saturated amides include octylamide which has 8 carbon atoms through stearylamide which has 18 carbon atoms. Preferred are laurylamide which contains 12 carbon atoms through myristylamide which contains 14 carbon atoms. The unsaturated amides include such olefinic monoamides as octenoic amide which has 8 carbon atoms through oleic amide which has 18 carbon atoms, preferably those having 12 to 14 carbon atoms. The aliphatic monoamines of 10 to 16 carbon atoms may be saturated or unsaturated. The saturated amines include decylamine which has 10 carbon atoms through hexadecylamine which has 16 carbon atoms, and preferably are decylamine having 10 carbon atoms through dodecylamine which contains 12 carbon atoms. The unsaturated amines include such olefinic amines as decenyl amine which has 10 carbon atoms through hexadecenyl amine which has 16 carbon atoms, preferably those having 10 to 12 carbon atoms.

The aforementioned absorption promoters may be used either alone or in combination. In the present invention, such absorption promoter or promoters can be effectively used in a proportion of at least 1/100 weight part to 1 weight part of molsidomine and preferably used in a proportion of at least 1/10 weight part. While the proportion of such absorption promoters in the entire pharmaceutical preparation cannot be specified in general terms, it is preferably not less than 0.1% by weight, more preferably 1 to 40% by weight. The proportion of molsidomine in the pharmaceutical preparation according to this invention is generally 0.1 to 40% by weight, preferably 1 to 30% by weight, and 5 to 100 mg per dose unit.

The percutaneous pharmaceutical preparation can be produced by compounding or mixing with a absorption promoter.

In addition to said absorption promoter, the pharmaceutical preparation according to this invention can be compounded with a base component, any of alcohols such as benzylalcohol, propylene glycol, sorbitol solution, glycerin, polyethylene glycol, etc., vegetable oils and fats such as olive oil, safflower oil, cottonseed oil, etc., animal oils and fats such as squalene, squalane, lanolin, etc., paraffins such as liquid paraffin, vaseline, etc., higher fatty acid esters such as isopropyl myristate, isopropyl palmitate, diethyl sebacate, glycerin ester such as monoacetin, diacetin, capryltriglyceride, caprintriglyceride, etc., or/and ethyl cellosolve, methyl cellosolve, etc. in suitable proportions, although the preferred proportion of such base component is generally 10 to 95% by weight.

In addition to the absorption promoter and base component mentioned above, the pharmaceutical preparation for percutaneous absorption according to this invention may contain a component for controlling the percutaneous absorption of molsidomine to thereby ensure a sustained blood concentration, such as solid paraffin, bee's wax, carnauba wax, hydrogenated castor oil, lanolin, polyethylene glycol (e.g. PEG 400, 1500, 4000), sperm wax, glyceryl monostearate, cholesterol, carbopol, carboxymethylcellulose, carboxyethylcellulose, silicone resin, etc., in suitable proportions, although the preferred proportion of such controlling component is generally 10 to 95% by weight.

In accordance with this invention, a pharmaceutical composition for percutaneous absorption containing the aforementioned components can be applied to the human body surface, either as it is or as formulated into any of the hydrophilic, oleagenous and emulsion forms mentioned in the Japanese Pharmacopeia. Or the pharmaceutical composition can be absorbed or deposited on a suitable support material and applied to the skin in such application forms as adhesive tape, sheet, patch or the like.

The support material mentioned just above is exemplified by high polymer film such as polyethylene, polypropylene, polyvinyl chloride, polyethylene terephthalate, polytetrafluoro-ethylene cellulose acetate, cellulose nitrate, polyacrylonitrile, ethylene-venylalcohol copolymer and polydimethylsiloxane, woven fabric, nonwoven fabric made of, for example, nylone, polyester, polypropylene and polyethylene, paper and so forth. When the composition is made available in the form of an adhesive tape, sheet or patch, the adhesive agent may be selected from among materials of polyalkylvinylether, polyalkyl acrylate, polyisobutylene, natural rubber, synthetic rubber and other type. Further, for the purpose of imparting suitable degrees of plasticity and adhesivity, it is possible to add animal or vegetable oil, vaselin, lanolin or the like, or/and, as an antieruption component, an antihistaminic agent such as diphenhydramine, etc.

As stated in detail hereinbefore, the pharmaceutical preparation for percutaneous absorption according to this invention is characterized in that after mere application to the human skin, its pharmacological effects are sustained for a prolonged time with the side effects being mitigated.

The invention will be described in further detail by way of examples which, however, should no means be construed as limiting the scope of the invention.

EXAMPLE 1

The components indicated in Table 1 were mixed and dissolved to prepare coating samples A through D.

Five male SD-JCL rats with a mean body weight of 250 g were anesthetized with pentobarbital and the abdominal hairs were clipped with an electric clipper (20 cm$^2$ 5×4 cm). Each of coating samples A though D was then coated on the clipped area. At 1, 2, 4 and 6 hours after application (till 8 hours for evaluation of sustained effect), 0.5 ml of venous blood was collected from the tail vain of each rat and the plasma concentration of molsidomine was determined by the following procedure.

Determination of plasma concentration of molsidomine

The venous blood sample was centrifuged and the plasma was separated. A 0.2 ml portion of the plasma was extracted with 1 ml of water and 5 ml of chloroform, and from 4 ml of the chloroform layer, the chloroform was evaporated. The residue was dissolved in 0.2 ml of a mixture of 0.05 M sodium acetate, acetonitrile and tetrahydrofuran (70:30:0.2, v/v), and 50 μl of the solution was subjected to liquid chromatography. The column used was μ-Bondapak C$_{18}$.

Evaluation of percutaneous absorption

The percutaneous absorption characteristic of molsidomine was evaluated in terms of $AUC_0{}^6$, area under the plasma concentration-time curve up 6 hours after administration. The sustained effect of molsidomine was evaluated by investigating the number of hours during which the concentration of molsidomine in the rat plasma remained at a level not less than 1 μg/ml. The results are set forth in Table 1.

TABLE 1

|  | Sample code | | | |
|---|---|---|---|---|
|  | A | B | C | D |
| Component (mg) | | | | |
| Molsidomine | 10 | 10 | 10 | 10 |
| Oleic acid | 20 | | | |
| Isopropyl myristate | | | 40 | |
| Isopropyl palmitate | | | | 40 |
| Propylene glycol | 170 | 190 | 150 | 150 |
| Percutaneous absorption results | | | | |
| $AUC_0^6$ value (μg · hr/ml) | 40.3 | 2.5 | 0 | 0 |
| Period for which plasma concentration is maintained not lower than 1 μg/ml (hr.) | 4 | 0 | 0 | 0 |

It is apparent from Table 1 that the $AUC_o^6$ value of 40.3 μg hr/ml for sample A of this invention was 15.9 times as large as the $AUC_o^6$ value of 2.5 μg hr/ml for sample B which contained no absorption promoter. In the duration of effective plasma concentration, also, sample A was by far superior to sample B.

In the case of samples C and D, in which isopropyl myristate and isopropyl palmitate were respectively used in lieu of the oleic acid in Sample A, molsidomine was not detected in the rat plasma. It was thus found that even higher fatty acids did not promote the percutaneous absorption of molsidomine when they were used in the form of esters.

REFERENCE EXAMPLE 1

In a mixture of 20 mg of lauric acid, which is a percutaneous absorption promotor according to this invention, and 177 mg of propylene glycol was dissolved 3 mg of clonidine to prepare a coating sample. Using this sample, a percutaneous absorption test was conducted in the same manner as Example 1. The plasma concentration of clonidine was determined by the following procedure.

The venous blood was centrifuged and the plasma was separated. A 0.2 ml of the plasma was extracted with 1 ml of 0.01 N NaOH and 5 ml of chloroform, and from 4 ml of the chloroform layer, the chloroform was evaporated. The residue was dissolved in 0.2 ml of a mixture of 0.05 M sodium acetate, acetonitrile and tetrahydrofuran (70:30:0.2, v/v), and 50 μl of this solution was subjected to liquid chromatography to determine the clonidine concentration. A column of μ-Bondapak $C_{18}$ was employed. The evaluation of percutaneous absorption was carried out in the same manner as described in Example 1. It was found that clonidine was not detected in the blood, indicating that lauric acid which is a percutaneous absorption promoter used in this invention is not effective in the case of clonidine. Similar tests were conducted using oleic acid, lauryl alcohol, oleinamide and laurylamine as well but all of them were ineffective for clonidine as was lauric acid.

EXAMPLE 2

In a mixture of 30 mg of lauric acid, which is a percutaneous absorption promoter according to this invention, and 160 mg of propylene glycol 160 was dissolved 10 mg of molsidomine to prepare a coating sample. The percutaneous absorption test in rats, determination of the blood concentration of molsidomine, and the evaluation of percutaneous absorption characteristics were all conducted in the same manner as Example 1. The $AUC_o^6$ value of the above sample was 35.0 μg hr/ml, which was 14 times as large as the $AUC_o^6$ value of sample B in Example 1, indicating that the sample according to this example offers a remarkably enhanced percutaneous absorption. Moreover, the percutaneous absorption effect of the above composition lasted for 5 hours.

EXAMPLE 3

In a mixture of 20 mg of lauryl alcohol, which is a percutaneous absorption promoter according to this invention, and 170 mg of polyethylene glycol 400 was dissolved 10 mg of molsidomine to prepare a coating sample. The percutaneous absorption test in rats, determination of the blood concentration of molsidomine, and the evaluation of percutaneous absorption characteristics were all conducted in the same manner as Example 1. The $ACU_o^6$ value of 31.3 μg hr/ml for this preparation was 12.5 times as large as the $AUC_o^6$ value for sample B of Example 1, indicating a remarkably enhanced percutaneous absorption. The percutaneous absorption effect of this preparation lasted for 5 hours.

EXAMPLE 4

20 mg of molsidomine was dissolved in a mixture of 40 mg of oleic acid, which is a percutaneous absorption promoter according to this invention, and 340 mg of lanolin under warming (60° C.) and the solution was gradually cooled to give a coating sample. The percutaneous absorption test in rats, determination of the blood concentration of molsidomine and the evaluation of percutaneous absorption characteristics were all conducted in the same manner as Example 1. The $AUC_o^6$ value of 20.0 g hr/ml for the above preparation was 8 times as large as the $AUC_o^6$ value for sample B of Example 1, indicating a remarkably enhanced absorption. Moreover, the percutaneous absorption effect of the preparation lasted for more than 8 hours.

EXAMPLE 5

20 mg of molsidomine was dissolved in a mixture of 40 mg of oleic acid, which is a percutaneous absorption promoter according to this invention, and 340 mg of polyethylene glycol 1500 under warming, and the solution was gradually cooled to give a coating sample. The percutaneous absorption test in rats, determination of the blood concentration of molsidomine, and the evaluation of percutaneous absorption characteristics were all conducted in the same manner as Example 1. The $ACU_o^6$ value of 22.8 μg hr/ml for this preparation was 9.1 times as large as the $AUC_o^6$ value of sample B, indicating a remarkably enhanced absorption. Moreover, the percutaneous absorption effect of the preparation lasted for more than 8 hours.

EXAMPLE 6

The components indicated below in Table 2 were mixed and dissolved to prepare coating samples E through U. For each of samples E through U, the blood concentration and sustained effect were evaluated in accordance with the methods described in Example 1. The results are set forth in Table 2.

TABLE 2

| | Sample |

TABLE 2-continued

|  |  |  | E | F | G | H | I | J | K | L | M |
|---|---|---|---|---|---|---|---|---|---|---|---|
| Component (mg) | active component | molsidomine | 10 | 30 | 10 | 15 | 30 | 20 | 10 | 10 | 10 |
|  | absorption promoter | valeric acid | 30 |  |  |  |  |  |  |  |  |
|  |  | stearic acid |  |  | 30 |  |  |  |  |  |  |
|  |  | oleic acid |  |  |  | 0.2 |  |  |  |  |  |
|  |  | cerotic acid |  |  |  |  | 20 |  |  |  |  |
|  |  | decenoic acid |  |  |  |  |  | 30 |  |  |  |
|  |  | gadoleic acid |  |  |  |  |  |  | 20 |  |  |
|  |  | decanol-1 |  |  |  |  |  |  |  | 20 |  |
|  |  | lauryl alcohol |  |  |  |  |  |  |  | 15 |  |
|  |  | oleic alcohol |  |  |  |  |  |  |  |  | 20 |
|  |  | cetyl alcohol |  |  |  |  |  |  |  |  |  |
|  |  | eicosanol |  |  |  |  |  |  |  |  |  |
|  |  | octylamide |  |  |  |  |  |  |  |  |  |
|  |  | oleicamide |  |  |  |  |  |  |  |  |  |
|  |  | palmitylamine |  |  |  |  |  |  |  |  |  |
|  |  | decylamine |  |  |  |  |  |  |  |  |  |
|  |  | laurylamine |  |  |  |  |  |  |  |  |  |
|  |  | tridecylamine |  |  |  |  |  |  |  |  |  |
|  | pharmaceutical basis | polyethylene glycol 400 |  |  |  |  |  |  |  | 110 |  |
|  |  | polyethylene glycol 1500 |  |  |  |  | 240 |  |  |  |  |
|  |  | propylene glycol | 160 |  | 189.8 | 165 |  | 160 | 170 | 50 | 170 |
|  |  | lanoline |  | 240 |  |  |  |  |  |  |  |
| percutaneous absorption | $AUC_0^6$ valve (μg hr/ml) |  | 18.7 | 32.4 | 12.6 | 10.9 | 22.1 | 26.5 | 30.4 | 26.3 | 15.7 |
|  | Period for which plasma concentration is maintained not lower than 1 μg/ml (hr) |  | 3.5 | >8 | 3 | 3 | >8 | 4 | 4 | 4 | 4 |

|  |  |  | Sample | | | | | | | |
|---|---|---|---|---|---|---|---|---|---|---|
|  |  |  | N | O | P | Q | R | S | T | U |
| Component (mg) | active component | molsidomine | 30 | 10 | 40 | 10 | 10 | 25 | 10 | 50 |
|  | absorption promoter | valeric acid |  |  |  |  |  |  |  |  |
|  |  | stearic acid |  |  |  |  |  |  |  |  |
|  |  | oleic acid |  |  |  |  |  |  |  |  |
|  |  | cerotic acid |  |  |  |  |  |  |  |  |
|  |  | decenoic acid |  |  |  |  |  |  |  |  |
|  |  | gadoleic acid |  |  |  |  |  |  |  |  |
|  |  | decanol-1 |  |  |  |  |  |  |  |  |
|  |  | lauryl alcohol |  |  |  |  |  |  |  |  |
|  |  | oleic alcohol |  |  |  |  |  |  |  |  |
|  |  | cetyl alcohol | 30 |  |  |  |  |  |  |  |
|  |  | eicosanol |  | 20 |  |  |  |  |  |  |
|  |  | octylamide |  |  | 30 |  |  |  |  |  |
|  |  | oleicamide |  |  |  | 20 |  |  |  |  |
|  |  | palmitylamine |  |  |  |  | 20 |  |  |  |
|  |  | decylamine |  |  |  |  |  | 20 |  |  |
|  |  | laurylamine |  |  |  |  |  |  | 20 |  |
|  |  | tridecylamine |  |  |  |  |  |  |  | 20 |
|  | pharmaceutical basis | polyethylene glycol 400 |  |  |  | 80 |  |  | 70 |  |
|  |  | polyethylene glycol 1500 |  |  |  | 90 |  |  |  | 230 |
|  |  | propylene glycol |  | 170 | 130 | 80 | 170 | 165 | 100 |  |
|  |  | lanoline | 240 |  |  |  |  |  |  |  |
| percutaneous absorption | $AUC_0^6$ valve (μg hr/ml) |  | 25.6 | 19.0 | 36.8 | 18.1 | 8.9 | 17.3 | 20.4 | 15.9 |
|  | Period for which plasma concentration is maintained not lower than 1 μg/ml (hr) |  | >8 | 3.5 | 4 | 5 | 3 | 3.5 | 4 | >8 |

EXAMPLE 7

Preparation of Patch

Fifty mg of molsidomine was added to a mixture solution of 20 mg of oleic acid and 1930 mg of propylene glycol and dissolved thoroughly to give a percutaneous absorption pharmaceutical composition.

A container having a size of 5 cm×6 cm and having an opening at one side was prepared by heat-sealing a polyethylenelaminated aluminum foil as a backing and a high-density polyethylene film (Highpore® 2200, Asahi Chemical Industry Co., Ltd.) as a rate controlling membrane for molsidomine in the composition.

A sheet of non-woven fabric made from polypropylene having a 2mm thickness and 5cm×4cm size was inserted into the container into which was poured 2 g of the above-mentioned composition.

The container was heat-sealed at the opening part and trimmed, and this trimmed part was coated with an acryltype adhesive agent for a pressure sensitive contact adhesive, followed by joining the coated part with a protective peel strip to prepare a patch.

By applying the thus-prepared patch onto a site of breast, abdomen or back of a patient, a given amount of molsidomine can be absorbed through the skin to allow its pharmacological effects to be sustained for a long time period.

EXAMPLE 8

Preparation of Tape

To a mixture solution of 100 mg of lauric acid, 1000 mg of polyethylene glycol 400 and 800 mg of propylene glycol was added 100 mg of molsidomine. The whole mixture was stirred at room temperature to become a complete composition for a percutaneous absorption pharmaceutical composition.

In 10 ml chloroform was dissolved 6 g of ethylene-vinylacetate copolymer, the content of the latter being 28 weight %, to which was added 2 g of the solution containing 100 mg of molsidomine. The mixture was spread on a polyethylene film to allow its thickness after drying to become 100 μm.

After drying, the surface was covered with a protective peel strip and cut it into a desired size to prepare a tape.

By applying the thus-prepared tape onto a site of breast, abdomen or back of a patient, a given amount of molsidomine is absorbed through the skin to allow its pharmacological effects to be sustained for a long time period.

EXAMPLE 9

Preparation of Patch

To a mixture of 200 mg of oleic acid, 600 mg of propylene glycol, 500 mg of polyethylene glycol 1500 and 600 mg of monoacetin was added 100 mg of molsidomene. The whole mixture was heated to give a solution.

A container having a size of 5cm×6xm was prepared by heat-sealing a polypropylene-laminated aluminium foil as a backing and a polypropylene film (DURA-GARD 2400 ®; Polyplastic Co. Ltd.). To this container was poured 2 g of the abovementioned solution. The container was heat-sealed at opening part to give a patch preparation according to a manner similar to that of Example 7. On to thus patch preparation was spread an acryl-type adhesive agent with a thickness of about 10 μm, which was covered with a protective peel strip to prepare an object composition.

By applying the thus-prepared patch onto a site of breast, abdomen or back of a patient, a given amount of molsidomine is absorbed through the skin to allow its pharmacological effects to be sustained for a long time period.

EXAMPLE 10

Preparation of Patch

A mixture of 50 mg of lauric acid, 200 mg of propylene glycol, 700 mg of polyethylene glycol 400 and 850 mg of polyethylene glycol 4000 was melted- by heating at 90° C., to which was dissolved 200 mg of molsidomine.

Onto a non-wovenn fabric of 5cm×4cm in size mad of polypropylene was spread evenly 2 g of the above-mentioned solution, which was fixed on a backing.

The thus-prepared composition was trimmed, and this trimmed part was coated with an acryl-type adhesive agent, for a contact adhesive followed by joining the coated part with a protective peel strip to prepare a patch.

What is claimed is:

1. A percutanneous pharmaceutical preparation for external application which comprises
    (a) N-ethoxycarbonyl-3-morpholinosydnonimine; and
    (b) at least 0.01 weight part of an absorption promoter per weight part of (a) which promoter is an aliphatic monocarboxylic acid of 5 to 30 carbons.

2. A percutaneous pharmaceutical preparation claimed in claim 1, wherein the proportion of N-ethoxyoarbonyl-3morpholinosydnonimine and the absorption promoter to the whole preparation are 0.1 to 40% by weight and more than 0.1% by weight, respectively.

3. A percutaneous pharmaceutical preparation for external application of claim 1 wherein said absorption prometer is oleic acid.

4. A percutaneous pharmaceutical drug delivery system which comprises a support material having adhered or deposited thereon a preparation for external application which comprises
    (a) N-ethoxycarbonyl-3-morpholinosydnonimine; and
    (b) at least 0.01 weight part of an absorption propmoter per weight part of (a) which promoter is an aliphatic monocarboxylic acid of 5 to 30 carbons.

5. A method of percutaneously administering a vasodilator effect to a patient which comprises the percutaneous administration of N-ethoxycarbonyl-3-morpholinosydnonimine as 0.01 weight part absorption promoter per part of said vasodilator, said absorption promoter being an aliphatic monocarboxylic acid of 5 to 30 carbons.

* * * * *